United States Patent [19]

Weckenmann et al.

[11] Patent Number: 5,648,092

[45] Date of Patent: Jul. 15, 1997

[54] SUCRALFATE CHEWABLE TABLET

[75] Inventors: Hans Peter Weckenmann; Hans-Günther Schwamb, both of Darmstadt, Germany

[73] Assignee: Merck Patent Gesellschaft Mit Beschrankter Haftung, Darmstadt, Germany

[21] Appl. No.: 732,523

[22] Filed: Jul. 19, 1991

[30] Foreign Application Priority Data

Jul. 19, 1990 [DE] Germany ............... 40 22 944.0

[51] Int. Cl.[6] .................................. A61K 9/34

[52] U.S. Cl. ............ 424/464; 424/465; 514/925; 514/926; 514/927; 514/960

[58] Field of Search ............... 424/464, 465, 424/474, 479, 480, 481; 514/925, 926, 927, 960, 961, 974

[56] References Cited

U.S. PATENT DOCUMENTS

| | | | |
|---|---|---|---|
| 4,885,281 | 12/1989 | Hanstein et al. | 514/53 |
| 4,910,023 | 3/1990 | Botzolakis et al. | 424/470 |
| 4,975,281 | 12/1990 | Harwood et al. | 424/441 |
| 4,983,392 | 1/1991 | Robinson | 424/434 |
| 4,990,610 | 2/1991 | Lazaridis et al. | 536/118 |
| 5,013,557 | 5/1991 | Tai | 424/493 |
| 5,122,598 | 6/1992 | della Valle et al. | 536/20 |

FOREIGN PATENT DOCUMENTS

WO89/07932  9/1989  WIPO.

*Primary Examiner*—John C. Bleutge
*Assistant Examiner*—Robert H. Harrison
*Attorney, Agent, or Firm*—Millen, White, Zelano & Branigan, P.C.

[57] ABSTRACT

The invention relates to pharmaceutical compositions in the form of pleasant-tasting chewable tablets or chewable coated tablets which, besides the pharmaceutically active ingredient sucralfate, essentially contain at least one rapidly swellable physiologically acceptable gel former plus sugars or sugar substitutes.

13 Claims, No Drawings

SUCRALFATE CHEWABLE TABLET

BACKGROUND OF THE INVENTION

The invention relates to pharmaceutical compositions in the form of chewable tablets or chewable coated tablets which contain sucralfate as pharmaceutical active ingredient.

Sucralfate (Ulcogant®) is a basic aluminum sucrose sulfate. It is disclosed in DE-A 1,568,346 and is employed in human medicine for the therapy of duodenal ulcer and to prevent the recurrence thereof, of gastric ulcer and of reflux esophagitis. In addition, an advantageous action of sucralfate in the treatment of emesis and/or diarrhea in veterinary medicine is described in DE-A 3,322,078.

The action of sucralfate is primarily explained by pepsin-binding and antacid effects. Sucralfate is very well tolerated and displays its action in the acid medium of the digestive tract, especially at pH values below 4, in which case it coats the mucous membranes of the stomach and duodenum with a protective layer. A preferred binding capacity to areas of the mucous membrane which have been attacked provides increased protection there, resulting in an increased rate of ulcer healing and a regeneration of the mucous membrane and its functions.

Sucralfate-containing compositions have to date mainly been used in the form of solid dosage forms such as powders or granules which can be suspended in water, or in liquid dosage forms such as stable, non-sedimentable suspensions as are disclosed in DE-A 3,430,809. U.S. Pat. No. 4,684,534 also discloses sucralfate-containing tablets. Tablets or coated tablets which are swallowed unchewed cannot be employed in practice. The tablets which would be necessary are too large and are otherwise impossible to take because of the relatively high single dose of about one gram of active ingredient. When the tablets are smaller and have a correspondingly reduced amount of sucralfate, the number of tablets would have to be greatly increased in order to achieve the required daily dose. However, this is to be regarded as extremely inconvenient. Moreover, there is a continual dependence on water or beverages. The drug form which is simplest to take is tablets which can be slowly chewed or allowed to dissolve in the mouth. They have the advantage compared with granules or powders that liquid media can be dispensed with, and compared with ready-prepared suspensions, they save considerably more space and weight and thus can be transported considerably better.

However, chewable tablets or coated tablets have not to date been able to achieve market acceptance. The probable reason is evidently the fact that such tablets have an unpleasantly flat, irritating and sandy taste, even though relatively large amounts of water-soluble auxiliaries, especially sugar or sugar substitutes and flavorings, have been added to tablets or coated tablets, because of the sparing solubility of sucralfate. In addition, the requisite high content of water-soluble auxiliaries means that sucralfate-containing chewable tablets of the prior art often have a size, e.g., 2 grams and above, which is unacceptable, especially for children.

SUMMARY OF THE INVENTION

It is an object of the invention to develop a pleasant-tasting sucralfate-containing chewable tablet of acceptable size, in which, moreover, the content of sugar or sweeteners can be minimized for dietetic or other health-impairing reasons without altering disadvantageously the taste or the solubility of the active ingredient.

Upon further study of the specification and appended claims, further objects and advantages of this invention will become apparent to those skilled in the art.

It has now been found that appropriate advantageous chewable tablets or chewable coated tablets can be obtained when swellable gel formers are added, in an amount between about 1 and 10% of that of sucralfate, to the active ingredient/auxiliary mixture.

In addition, the use of physiologically acceptable gel formers means that the amount of sugar or sugar substitutes can be reduced by up to 75%. When the tablets or coated tablets according to the invention are chewed or sucked, the saliva penetrating into the chewable tablet is spontaneously thickened so that an easily swallowed and surprisingly pleasant-tasting suspension with a creamy consistency is produced. On tabletting, the pharmaceutical compositions according to the invention display only low brittleness. The use of gel formers, especially xanthan gum, in sucralfate-containing suspensions is described in DE-A 3,430,809. However, they were used therein merely as stabilizer for the appropriate suspensions. Otherwise, the said gel formers are known to be used to increase the viscosity of liquids, suspensions or pastes.

The invention relates to a pharmaceutical composition in the form of sucralfate-containing chewable tablets or chewable coated tablets, characterized in that it contains at least one physiologically acceptable gel former.

The invention particularly relates to a corresponding pharmaceutical composition which additionally contains at least one sugar and/or sugar substitute or mixtures thereof.

The invention furthermore relates to a process for producing a pharmaceutical composition, characterized in that sucralfate is mixed with at least one gel former and at least one sugar or sugar substitute and/or auxiliaries and/or excipients and is compressed to tablets with an average tensile strength of 40–120 newtons.

Suitable gel formers for use in this invention include all those physiologically acceptable compounds known for this function in the prior art, including those disclosed in the foregoing reference, especially those which swell to a degree of 1.5 to 5 times original volume rapidly, e.g., in 10 to 60 seconds. Many are also disclosed in "Gums and Stabilizers for Food Industry 3," Phillips, Wedlock, Williams, 1986, Elsevier Science Publishing, New York.

Particularly suitable gel formers in the pharmaceutical compositions according to the invention are high molecular weight polysaccharides or cellulose derivatives because they usually swell sufficiently and rapidly and are physiologically well tolerated.

Examples of such suitable gel formers are xanthan gum, methylcelluloses such as sodium carboxymethylcellulose or hydroxypropylmethylcellulose, hydroxyethylcellulose, hydroxypropylcellulose, alginates, tragacanth or soluble starch. These substances are all commercially available and usually meet the purity requirements and quality regulations for pharmaceutical products. Particularly preferred gel formers as components in the pharmaceutical compositions according to the invention are xanthan gum, sodium carboxymethylcellulose and methylcelluloses, especially hydroxypropylmethylcellulose. It is also possible to employ different gel formers. In this case mixtures of hydroxypropylmethylcellulose and xanthan gum or of sodium carboxymethylcellulose and xanthan gum are particularly suitable.

The amount of gel formers based on the sucralfate active ingredient can vary according to the invention between 0.5 and 20% (w/w), preferably between 2 and 10%. Thus, with an average dose of active ingredient of 1000 mg/tablet, preferably between 20 and 100 mg of gel former are required.

The sucralfate used for producing the sucralfate chewable tablet according to the invention is a conventional, commercially available active ingredient. Sucralfate is employed in finely ground form with a particle size of preferably below 50 μm. About 750 to 1,250 mg, preferably, 1,000 mg of sucralfate are employed per tablet.

According to the invention, the chewable tablets preferably additionally contain water-soluble sugars and/or sugar substitutes. Suitable water-soluble sugars and/or sugar substitutes are glucose, maltose, sucrose, dextrose, fructose, sorbitol, mannitol or other types of natural or artificial sweeteners. Preferred substances are sorbitol and mannitol. Mixtures of various sugars or sugar substitutes are also suitable.

The sucralfate/sugar ratio in known tablets must be about 1:1 in order to obtain a tablet which is palatable. According to the invention, it is possible to distinctly reduce the sugar/sugar substitute content in the tablets without crucially impairing the taste or the saliva solubility behavior. However, a low sugar content is extremely desirable for dietetic reasons or for preventing caries.

According to the invention, the preferred sucralfate/sugar ratio in the chewable tablets is from 2:1 to 10:1, which corresponds to about 100 to 350 mg of sugar per tablet. It is also possible to employ larger amounts of sucralfate/sugar ratio.

It is possible, where appropriate, to add natural or synthetic flavorings, fragrances, auxiliaries and excipients such as, for example, magnesium stearate or glycerol tristearate. The proportion of these substances in the total amount of the tablet preferably varies between about 2 and 8% (w/w).

It is also possible to add other active ingredients to the sucralfate chewable tablets according to the invention. Suitable ingredients, which are known to be combinable with sucralfate, are, for example, antacids, spasmolytics, antiflatulents, $\beta_2$ receptor blockers, non-steroidal antirheumatics and generally drugs which inhibit acid secretion. These also include the amino acids described in EP 107,209, which enhance the action of sucralfate in coating mucous membranes.

The range of medical uses of the sucralfate chewable tablet according to the invention is entirely analogous to the known dosage forms of sucralfate which is well known in the art.

The pharmaceutical compositions according to the invention can be produced as follows, for example: first, granules are produced from sucralfate particles with, preferably, sugar or sugar substitute or another water-soluble excipient by known and customary methods, some of which are used on the industrial scale.

Thus, for example, sugar or a sugar mixture is dissolved in water, and the sugar solution is sprayed onto sucralfate particles (about 20–50 μm) in a commercially available granulator at 50°–80° C. The active ingredient granulated in accordance with the above is preferably screened (about 40–60 mesh/cm$^2$) and vigorously mixed with the gel former or the mixture of gel formers and where appropriate, together with other components such as flavorings and/or auxiliaries or excipients. The mixture is thereafter ready for compression and is subsequently tabletted with a commercially available tabletting press. The compression pressure is such that the resulting chewable tablets have an average tensile strength of 40 to 120 newtons, preferably 60–100 newtons. The mechanical properties of the tablets produced in accordance with the invention are surprisingly more advantageous as compared with those tablets produced according to the prior art without gel formers.

To produce chewable coated tablets, the produced tablets are provided with a coating by customary processes and using customary substances and agents well known in the art. Possible compositions of such suitable coatings are found in Example 3.

The use of gel formers for chewable tablets with other insoluble pharmaceutically active ingredients where high doses are required, such as, for example, calcium phosphate, is generally also exceptionally suitable for achieving the advantageous properties described above, especially taste and saliva solubility behavior.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The entire disclosures of all applications, patents and publications, if any, cited above and below, and of corresponding application Federal Republic of Germany P 40 22 944.0, filed Jul. 19, 1990, are hereby incorporated by reference.

EXAMPLES

Example 1

3.605 kg of sucrose are dissolved in 6 liters of water and sprayed onto 10 kg of sucralfate in a fluidized bed granulator at 70° C. and dried until the outlet temperature is 50° C. The sucralfate coated in accordance with the invention was screened with a screen of about 45 mesh/cm$^2$ and vigorously mixed with 0.240 kg of xanthan gum and with 0.150 kg of magnesium stearate and 0.150 kg of glycerol tristearate and 15 g of peppermint flavor. The mixture ready for compression was now tabletted using a rotary press with a pressure such that the chewable tablets have an average tensile strength of about 100 newtons. Tablets of the following composition were 15 produced:

| | |
|---|---|
| sucralfate | 1000.0 mg |
| sucrose | 360.5 mg |
| xanthan gum | 24.0 mg |
| magnesium stearate | 15.0 mg |
| glycerol tristearate | 15.0 mg |
| peppermint flavor | 1.5 mg |

Example 2

Chewable tablets of the following composition were produced in analogy to Example 1 (data in mg):

| | | | |
|---|---|---|---|
| a) | sucralfate | 1000.0 | 1000.0 |
| | fructose | 360.5 | 650.0 |
| | xanthan gum | 24.0 | 24.0 |
| | hydroxypropylmethylcellulose | 10.0 | 15.0 |
| | magnesium stearate | 15.0 | 15.0 |
| | glycerol tristearate | 15.0 | 15.0 |
| | lemon flavor | 1.5 | 2.0 |

| | | | | |
|---|---|---|---|---|
| b) | sucralfate | 1000.0 | 1000.0 | 1000.0 |
| | mannitol | 360.0 | 100.0 | 650.0 |
| | xanthan gum | 100.0 | 25.0 | 4.0 |
| | hydroxypropylmethylcellulose | 10.0 | 10.0 | 15.0 |
| | magnesium stearate | 15.0 | 15.0 | 20.0 |
| | glycerol tristearate | 15.0 | 15.0 | 15.0 |
| | aspartame | 6.0 | 8.0 | 4.0 |
| | orange flavor | 1.5 | 1.5 | 2.0 |

-continued

| | | | | |
|---|---|---|---|---|
| c) | sucralfate | 1000.0 | 1000.0 | 1000.0 |
| | mannitol | 360.5 | 100.0 | 650.0 |
| | xanthan gum | 24.0 | 24.0 | 24.0 |
| | sodium carboxymethylcellulose | 10.0 | 10.0 | 25.0 |
| | magnesium stearate | 15.0 | 15.0 | 25.0 |
| | glycerol tristearate | 15.0 | 15.0 | 25.0 |
| | caramel flavor | 1.5 | 1.5 | 5.0 |
| | saccharin sodium | 2.0 | 2.0 | 1.0 |
| d) | sucralfate | 1000.0 | | 1000.0 |
| | sorbitol | 260.5 | | 325.0 |
| | sucrose | 100.0 | | 325.0 |
| | xanthan gum | 24.0 | | 24.0 |
| | hydroxypropylmethylcellulose | 10.0 | | 15.0 |
| | magnesium stearate | 15.0 | | 15.0 |
| | glycerol tristearate | 15.0 | | 15.0 |
| | peppermint flavor | 1.5 | | 2.0 |
| e) | sucralfate | 1000.0 | 1000.0 | 1000.0 |
| | mannitol | 600.0 | — | 300.0 |
| | sorbitol | — | 600.0 | 300.0 |
| | hydroxypropylmethylcellulose | 10.0 | 10.0 | 15.0 |
| | sodium carboxymethylcellulose | 15.0 | — | — |
| | sodium alginate | — | 25.0 | — |
| | tragacanth | — | — | 50.0 |
| | magnesium stearate | 15.0 | 15.0 | 15.0 |
| | glycerol tristearate | 15.0 | 15.0 | 15.0 |
| | caramel flavor | 1.5 | 1.5 | 1.5 |

Example 3

Tablet coatings of the following composition were prepared (data in mg):

| Subcoating | | |
|---|---|---|
| gelatin | 2.0 | 2.0 |
| gum arabic | 4.5 | 4.5 |
| sucrose | 69.0 | — |
| sorbitol | — | 24.0 |
| mannitol | — | 45.0 |
| talc | 37.0 | 37.0 |
| bolus alba | 45.0 | 45.0 |
| titanium dioxide | 22.5 | 22.5 |
| Main coating: | | |
| sucrose | 490.0 | — |
| sorbitol | — | 325.0 |
| mannitol | — | 165.0 |
| talc | 50.0 | 50.0 |
| titanium dioxide | 30.0 | 30.0 |
| carnauba wax | 2.0 | — |
| beeswax | — | 2.0 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical composition comprising sucralfate and at least one physiologically acceptable gel former, in the form of a chewable tablet or a chewable coated tablet, wherein the amount of said gel former is 0.5–20% (w/w) based on the amount of sucralfate.

2. A tablet of claim 1, wherein the dosage of sucralfate is 750–1,250 mg.

3. A tablet of claim 2, wherein said dosage is about 1,000 mg.

4. A pharmaceutical composition according to claim 2, further comprising an effective amount of a sugar, a sugar substitute or a mixture thereof.

5. A pharmaceutical composition according to claim 1, wherein the ratio between the sucralfate and the gel former is 10:1–100:1 by weight.

6. A pharmaceutical composition according to claim 1, wherein said gel former is selected from the group consisting of xanthan gum, hydroxypropylmethylcellulose, sodium carboxymethylcellulose, hydroxymethylcellulose, hydroxypropylcellulose and mixtures thereof.

7. A pharmaceutical composition according to claim 4, wherein the ratio between the sucralfate and the sugar or sugar substitute is 2:1–10:1 by weight.

8. A pharmaceutical composition according to claim 4, wherein the sugar substitute is sorbitol or mannitol.

9. A composition of claim 1, wherein the amount of gel former is 2–10% (w/w) based on the amount of sucralfate.

10. A composition according to claim 4, wherein said effective amount of sugar, sugar substitute or mixture thereof is 100–350 mg.

11. A composition according to claim 1, further comprising 2–8% (w/w) of additional agents selected from the group consisting of flavorings, fragrances, auxiliaries and mixtures thereof.

12. A composition according to claim 1, further comprising another active ingredient selected from the group consisting of antacids, spasmolytics, antiflatulents, $B_2$ receptors blockers, non steroidal antirheumatics and acid secretion inhibitors.

13. A pharmaceutical composition according to claim 1, wherein the gel former swells from about 1.5 to about 5 times its dry volume when contacted with an aqueous solution.

* * * * *